US00RE42327E

(19) United States
(12) Reissued Patent
Nakada et al.

(10) Patent Number: US RE42,327 E
(45) Date of Reissued Patent: May 3, 2011

(54) MEDICINAL COMPOSITIONS IMPROVING BRAIN FUNCTION AND METHOD FOR IMPROVING BRAIN FUNCTION

(75) Inventors: Yasushi Nakada, Harrison, NY (US); Masaya Nakagawa, Kamiichi (JP); Satoshi Ono, Toyama (JP)

(73) Assignee: Toyama Chemical Co., Ltd., Tokyo (JP)

(21) Appl. No.: 12/683,813

(22) PCT Filed: Apr. 3, 2003

(86) PCT No.: PCT/JP03/04292

§ 371 (c)(1),
(2), (4) Date: Dec. 13, 2004

(87) PCT Pub. No.: WO03/105830

PCT Pub. Date: Dec. 24, 2003

Related U.S. Patent Documents

Reissue of:
(64) Patent No.: 7,342,043
Issued: Mar. 11, 2008
Appl. No.: 10/516,320
Filed: Dec. 13, 2004

(30) Foreign Application Priority Data

Jun. 14, 2002 (JP) ..... 2002-173483

(51) Int. Cl.
*A61K 31/38* (2006.01)
(52) U.S. Cl. ..... 514/443; 514/315; 514/210.19
(58) Field of Classification Search ..... 514/443, 514/315, 210.19, 444
See application file for complete search history.

(56) References Cited

U.S. PATENT DOCUMENTS

| | | | | |
|---|---|---|---|---|
| 5,081,117 | A * | 1/1992 | Glamkowski et al. | 514/216 |
| 5,177,082 | A | 1/1993 | Yu et al. | |
| 6,797,726 | B1 * | 9/2004 | Ono et al. | 514/443 |
| 2005/0250843 | A1 | 11/2005 | Nakada et al. | |
| 2006/0205709 | A1 | 9/2006 | Kimura et al. | |
| 2008/0103126 | A1 | 5/2008 | Nakada et al. | |
| 2009/0093453 | A1 | 4/2009 | Iwakami et al. | |
| 2009/0111992 | A1 | 4/2009 | Saitoh et al. | |
| 2009/0209512 | A1 | 8/2009 | Iwakami et al. | |

FOREIGN PATENT DOCUMENTS

| | | | |
|---|---|---|---|
| CA | 2081808 | | 5/1993 |
| EP | 0 383 281 | | 8/1990 |
| EP | 1 186 594 | | 3/2002 |
| JP | 61-225158 | | 10/1986 |
| JP | 62-215527 | | 9/1987 |
| JP | 64-79151 | | 3/1989 |
| JP | 2-10827 | | 1/1990 |
| JP | 3-47158 | | 2/1991 |
| JP | 3-232830 | | 10/1991 |
| JP | 4-95070 | | 3/1992 |
| JP | 5-140149 | | 6/1993 |
| JP | 5-221877 | | 8/1993 |
| JP | 5-279355 | | 10/1993 |
| JP | 10-259126 | | 9/1998 |
| JP | 11-501014 | A | 1/1999 |
| JP | 11-514671 | A | 12/1999 |
| JP | 2000-500786 | A | 1/2000 |
| JP | 2000-501117 | A | 2/2000 |
| JP | 2001-523642 | | 11/2001 |
| WO | WO 92 18493 | | 10/1992 |
| WO | WO 96 12717 | | 5/1996 |
| WO | WO 96/26196 | A2 | 8/1996 |
| WO | WO 97/30703 | A1 | 8/1997 |
| WO | WO 98 01425 | | 1/1998 |
| WO | WO 98/01425 | A1 | 1/1998 |
| WO | WO 98 05292 | | 2/1998 |
| WO | WO 98/05292 | A2 | 2/1998 |
| WO | WO 98 06697 | | 2/1998 |
| WO | WO 98/06697 | A1 | 2/1998 |
| WO | WO 99 25363 | | 5/1999 |
| WO | WO 99 31056 | | 6/1999 |
| WO | WO 00 76957 | | 12/2000 |
| WO | WO 03 035647 | | 5/2003 |

OTHER PUBLICATIONS

Mealy et al., Drugs of the future, 2002, 27(9): 879-915.*
U.S. Appl. No. 12/683,813, filed Jan. 7, 2010, Nakada, et al.
U.S. Appl. No. 11/957,832, filed Dec. 17, 2007, Nakada, et al.
U.S. Appl. No. 12/253,379, filed Oct. 17, 2008, Saitoh, et al.
U.S. Appl. No. 10/553,120, filed Oct. 14, 2005, Kimura, et al.
U.S. Appl. No. 12/542,074, filed Aug. 17, 2009, Kimura, et al.
U.S. Appl. No. 12/298,656, filed Oct. 27, 2008, Iwakami, et al.
U.S. Appl. No. 12/370,736, filed Feb. 13, 2009, Iwakami, et al.
Shimada et al., 1997, CAS:127:362624.*
Ikeda, Ken et al. "T-588, a novel neuroprotective agent, delays progression of neuromuscular dysfunction in wobbler mouse motoneuron disease", Brain Research, vol. 858, No. 1, pp. 84-91 2000.

(Continued)

*Primary Examiner* — Rei-tsang Shiao
(74) *Attorney, Agent, or Firm* — Oblon, Spivak, McClelland, Maier & Neustadt, L.L.P.

(57) ABSTRACT

An alkyl ether derivative represented by the formula:

[1]

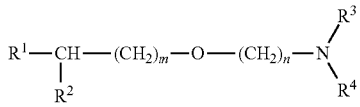

wherein $R^1$, $R^2$, $R^3$, $R^4$, m and n are as defined in the specification, or salts thereof exhibits synergistically improved anti-hypoxic activity when combined with a compound having an acetylcholine esterase inhibitory activity. Therefore, the combination according to the present invention is useful as a method for improving cerebral function. Further, a pharmaceutical composition containing the compound relating to the combination according to the present invention is useful for treatment and prevention of dysfunction of cerebral acetylcholine neurons in the sequelae of cerebrovascular dementia, senile dementia, Alzheimer's disease and ischemic cerebral lesion and in the cerebral apoplexy or the memory impairment caused by selective neuronal death.

8 Claims, No Drawings

OTHER PUBLICATIONS

Ono, Satoshi et al. "Protective Effect of R(−)-1-(Benzo[b]thiophen-5-yl)-2-[2-(N,N-diethylamino)ethoxy]ethanol Hydrochloride (T-588), a Novel Celebral Activator, against Experimental Cerebral Anoxia", Japan, J. Pharmacol., vol. 62, No. 1, pp. 81-86 1993.

Palmer, Gene C. et al. "The Low-Affinity, Use-Dependent NMDA Receptor Antagonist AR-R 15896AR", Annals New York Academy of Sciences, vol. 890, pp. 406-420 1999.

Ono, S. et al. "Effects of T-588, a novel cognitive enhancer, on acetylcholine and monoamine releases and second-messenger systems in rats", Society for Neuroscience, vol. 21, p. 947, #377.2 1995.

Ono, S. et al. "T-588, a novel cognition enhancer, protects cortical cell cultures against both beta-amyloid-and 4-hydroxy-2-nonenal-induced apoptosis", Society for Neuroscience, vol. 24, part 1, p. 228, #91.7 1998.

U.S. Appl. No. 11/416,321, filed May 3, 2006, Saitoh et al.

* cited by examiner

MEDICINAL COMPOSITIONS IMPROVING BRAIN FUNCTION AND METHOD FOR IMPROVING BRAIN FUNCTION

Matter enclosed in heavy brackets [ ] appears in the original patent but forms no part of this reissue specification; matter printed in italics indicates the additions made by reissue.

This application is a 371 of PCT/JP03/04292 filed on Apr. 3, 2003.

TECHNICAL FIELD

This invention relates to a pharmaceutical composition for improving the cerebral function which contains an alkyl ether derivative and a compound having acetylcholine esterase inhibiting activity, and to a method using an alkyl ether derivative in combination with a compound having acetylcholine esterase inhibiting activity for the purpose of. improving the cerebral function.

BACKGROUND ART

It is generally said that, in the sequela of cereblovascular diseases or various neuronal degenerative diseases, the dysfunction of cerebral neurons and the cerebral neuronal death are in a close relation. Particularly in the sequelae of cerebrovascular dementia, senile dementia, Alzheimer's disease and ischemic cerebral lesion and in the cerebral apoplexy, there appears memory impairment caused by a dysfunction of in-brain acetylcholine neurons or a selective neuronal death.

As drugs for symptomatic treatment of this memory impairment, for example, compounds having an acetylcholine esterase inhibiting activity such as Tacrine, Donepezil, and the like are used.

On the other hand, the anti-hypoxic activity is used for evaluating the neuroprotective activity in-vitro, and it is reported that, in the in-vivo experiments, too, compounds having a neuroprotective activity show the same effect as above [Ann. N. Y. Acad. Sci., Vol. 890, Pages 406-420, 1999]. Further, it has been reported that the anti-hypoxic activity is shown by compounds activating the in-brain acetylcholine neurons and by Tacrine (1,2,3,4-tetrahydro-9-acridinamine hydrochloride) showing an acetylcholine esterase inhibiting activity [Jpn. J. Pharmacol., Vol. 62, Pages 81-86, 1993].

Accordingly, a work for studying the in-vivo anti-hypoxic activity can be regarded as a method for evaluating the compounds having one of the neuroprotective effect and the in-brain acetylcholine neurons activating effect or both of these effects.

The 1,2-ethanediol derivatives or salts thereof described in JP 3-232830A and JP 4-95070A are compounds useful as a cerebral function-improving agent, and particularly (R)-1-{benzo[b]thiophen-5-yl}-2-[2-(N,N-diethylamino}ethoxy] ethanol hydrochloride (hereinafter, referred to as T-588) is a preferable compound. It has been reported that T-588 has an anti-hypoxic activity and an anti-amnestic activity, and promotes the release of in-brain acetylcholine (SOCIETY FOR NEUROSCIENCE, Abstracts, Vol. 21, Page 947, 1995). It is also known that T-588 exhibits a protecting effect on the neuronal death caused by amyloid-beta-protein (SOCIETY FOR NEUROSCIENCE, Abstracts, Vol. 24, Part 1, Page 228, 1998) and that T-588 exhibits an increasing effect on the action of nerve growth factor (WO96/12717). However, nothing has ever been reported with regard to the cerebral function improving action of T-588 and particularly to chemicals and method for improving the anti-hypoxic action thereof.

At the present time, compounds having a neuroprotective activity are being studied from the viewpoint of preventing the dysfunction of in-brain acetylcholine neurons or the selective neuronal death in the sequela of cerebrovascular dementia, senile dementia, Alzheimer's disease and ischemic cerebral lesion and in the cerebral apoplexy. However, the therapeutic effect of these compounds are not yet well known. Although acetylcholine esterase inhibiting drugs such as Tacrine, Donepezil, Galanthamine, and the like are commercially available as cerebral function-improving drugs including Alzheimer's disease-curing drug, these drugs have problems in the point of side-reactions because some of them have a hepatic toxicity and some others have a side reaction accompanied by activation of acetylcholine neurons other than central nervous system. Thus, for the purpose of lightening the side reaction of acetylcholine esterase inhibiting drugs, for example, a combination of a brain circulation metabolism improver such as Idebenone and an acetylcholine esterase inhibitor (JP 10-259126A) or a combination of a compound having a nerve growth factor-like activity (SR57746A) and an acetylcholine esterase inhibitor (WO99/25363), etc. are being attempted.

DISCLOSURE OF THE INVENTION

After extensive studies, the present inventors have found that the anti-hypoxic activity can synergistically be improved by using a compound having an acetylcholine esterase inhibiting activity in combination with an alkyl ether derivative represented by the following formula [1]:

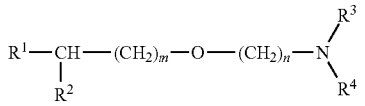

[1]

wherein $R^1$ represents a substituted or unsubstituted heterocyclic group; $R^2$ represents a hydrogen atom or a hydroxyl group; $R^3$ and $R^4$ which may be the same or different, each represents a substituted or unsubstituted alkyl, or $R^3$ and $R^4$, taken together with the nitrogen atom to which they are linked, form a substituted or unsubstituted cyclic amino group; m represents an integer of 1 to 5; and n represents an integer of 1 to 6; or a salt thereof, including T-588. Based on the knowledge that the combination of an alkyl ether derivative of formula [1] or a salt thereof and a compound having acetylcholine esterase inhibiting activity is useful as a method for improving the cerebral function, the present invention has been accomplished.

Next, the present invention will be explained in detail.

Unless otherwise referred to, the technical terms used in this specification have the following meanings. Halogen atom means a fluorine atom, a chlorine atom, a bromine atom or an iodine atom; alkyl group means a straight chain or branched chain $C_{1-12}$ alkyl group such as methyl, ethyl, propyl, isopropyl, butyl, isobutyl, tert-butyl, pentyl, hexyl, heptyl, octyl and the like; lower alkyl group means a straight chain or branched chain $C_{1-6}$ alkyl group such as methyl, ethyl, propyl, isopropyl, butyl, isobutyl, tert-butyl, pentyl, hexyl and the like; alkoxy group means a straight or branched chain $C_{1-12}$ alkyloxy group such as methoxy, ethoxy, propoxy, isopropoxy, butoxy, isobutoxy, tert-butoxy, pentyloxy, hexyloxy, heptyloxy, octyloxy and the like; lower alkyloxy group means a straight chain or branched chain $C_{1-6}$ alkyloxy group such as methoxy, ethoxy, propoxy, isopropoxy, butoxy, isobutoxy, tert-butoxy, pentyloxy, hexyloxy and the like; alkenyl group means a $C_{2-12}$ alkenyl group such as vinyl, propenyl, butenyl, pentenyl, hexenyl, heptenyl, octenyl and the like; lower alkenyl group means a $C_{2-6}$ alkenyl group such as vinyl, propenyl, butenyl, pentenyl, hexenyl and the like; alkenyloxy group means $C_{2-12}$ alkenyloxy group such as vinyloxy, propenyloxy, butenyloxy, pentenyloxy, hexenyloxy, heptenyloxy, octenyloxy and the like; lower alkenyloxy group means $C_{2-6}$ alkenyloxy group such as vinyloxy, propenyloxy, butenyloxy, pentenyloxy, hexenyloxy and the like; alkynyl group means $C_{2-6}$ alkynyl group such as ethynyl, propynyl, butynyl, pentynyl and the like; cycloalkyl group means cyclopropyl, cyclobutyl, cyclopentyl and cyclohexyl groups; alkylthio group means $C_{1-12}$ alkylthio groups such as methylthio, ethylthio, propylthio, isopropylthio, butylthio, isobutylthio, tert-butylthio, pentylthio, hexylthio, heptylthio, octylthio and the like; lower alkylthio group means $C_{1-6}$ alkylthio groups such as methylthio, ethylthio, propylthio, isopropylthio, butylthio, isobutylthio, tert-butylthio, pentylthio, hexylthio and the like; aryl group means phenyl, naphthyl, indanyl and indenyl; aryloxy group means phenyloxy, naphthyloxy, indanyloxy and indenyloxy groups; ar-lower alkyl group means ar-$C_{1-6}$ alkyl groups such as benzyl, diphenylmethyl, phenethyl and the like; ar-lower alkenyl group means ar-$C_{2-6}$ alkenyl groups such as cinnamyl and the like; ar-lower alkoxy group means ar-$C_{1-6}$ alkoxy group such as phenylmethyloxy, naphthylmethyloxy and the like; ar-lower alkylthio group means ar-$C_{1-6}$ alkylthio groups such as phenylmethylthio, naphthylmethylthio and the like; lower alkylenedioxy group means $C_{1-6}$ alkylenedioxy group such as methylenedioxy, ethylenedioxy and the like; lower acyl group means $C_{1-6}$ acyl groups such as formyl, acetyl, ethylcarbonyl and the like; aroyl group means arylcarbonyl groups such as benzoyl, naphthylcarbonyl and the like; ar-lower alkenoyl group means ar-$C_{2-6}$ alkenoyl groups such as cinnamoyl and the like; lower alkylsulfonyl group means $C_{1-6}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl and the like; arylsulfonyl group means phenylsulfonyl, p-toluenesulfonyl, naphthylsulfonyl and the like; lower alkylsulfonyloxy group means $C_{1-6}$ alkylsulfonyloxy groups methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, pentylsulfonyloxy and the like; arylsulfonyloxy group means phenylsulfonyloxy, p-toluenesulfonyloxy, naphthylsulfonyloxy groups and the like; ar-lower alkylsulfonyl group means ar-$C_{1-6}$ alkylsulfonyl groups such as benzylsulfonyl and the like; lower alkylsulfonylamino group means $C_{1-6}$ alkylsulfonylamino groups such as methylsulfonylamino, ethylsulfonylamino, propylsulfonylamino and the like; arylsulfonylamino group means phenylsulfonylamino, p-toluenesulfonylamino and naphthylsulfonylamino groups and the like; cyclic amino group means cyclic amino groups having 4-7 membered cycle, fused cycle or crosslinked cycle which contains at least one nitrogen atom as a hetero-atom constituting said ring and may additionally contain at least one oxygen atom or sulfur atom, such as azetidinyl, pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl and the like; heterocyclic group means the above-mentioned cyclic amino groups and, in addition, heterocyclic groups which may contain at least one hetero-atom selected from nitrogen, oxygen and sulfur atoms as a hetero-atom constituting said ring and have at least one 5- or 6-membered ring structure or a fused ring structure or a crosslinked ring structure, such as pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxolyl, 1,4-benodioxanyl and the like; and nitrogen-containing saturated 6-membered heterocyclic ring means saturated 6-membered rings containing nitrogen atom as a hetero-atom, such as piperidine, piperazine, perhydropyrimidine, perhydropyridazine and the like.

The heterocyclic group of $R^1$ may be substituted with at least one residue selected from halogen atom, optionally substituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino groups, or optionally protected amino group, optionally protected hydroxyl group, nitro group, heterocyclic group, oxo group, lower alkylenedioxy group and the like.

The amino groups of $R^3$ and $R^4$ and the cyclic amino group which $R^3$ and $R^4$ form in conjunction with the nitrogen atom to which $R^3$ and $R^4$ are linked may be substituted with at least one group selected from halogen atom, optionally substituted amino group, lower alkyl group, aryl group, ar-lower alkyl group, ar-lower alkenyl group, aroyl group, ar-lower alkenoyl group, heterocyclic group and the like.

The substituents in the above-mentioned $R^1$, $R^3$, $R^4$ and the cyclic amino group which $R^3$ and $R^4$ form in conjunction with the nitrogen atom to which $R^3$ and $R^4$ and linked may further be substituted with at least one group selected from halogen atom, optionally protected hydroxyl group, optionally protected carboxyl group, optionally protected amino group, lower alkyl group, lower alkoxy group, lower acyl group, cycloalkyl group, ar-lower alkyl group and the like.

The protecting group for carboxyl group includes all the residues which can conventionally be used as a protecting group for carboxyl group, of which examples include lower alkyl groups such as methyl, ethyl, propyl, isopropyl, 1,1-dimethylpropyl, butyl, tert-butyl and the like; aryl groups such as phenyl, naphthyl and the like; ar-lower alkyl groups such as benzyl, diphenylmethyl, trityl, p-nitrobenzyl, p-methoxybenzyl, bis(p-methoxyphenyl)methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichloroethyl and the like; lower alkylsilyl-lower alkyl groups such as 2-(trimethylsilyl)ethyl and the like; acyloxy-lower alkyl groups such as acetoxymethyl, propionyloxymethyl, pivaloyloxymethyl and the like; nitrogen-containing heterocycle-lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl)ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; etc.

The protecting group for hydroxyl group include all the residues which can conventionally be used for protection of hydroxyl group, of which examples include acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)-ethoxycarbonyl, 2-(phenylsulfonyl)ethoxycarbonyl, 2-(triphenylphosphonio) ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; lower alkoxy- and lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, 1-methyl-1-methoxyethyl and the like; lower alkyl- and aryl-sulfonyl groups such as methanesulfonyl, p-toluenesulfonyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; etc.

The protecting group for amino group include all the residues which can conventionally be used as a protecting group for amino groups, of which examples include acyl groups such as trichloroethoxycarbonyl, tribromoethoxycarbonyl, benzyloxycarbonyl, p-nitrobenzyloxycarbonyl, o-bromobenzyloxycarbonyl, (mono-, di- and tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-lower alkyl groups such as benzyl, diphenylmethyl, trityl and the like; arylthio groups such as 2-nitrophenylthio, 2,4-dinitrophenylthio and the like; alkyl- or arylsulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocycle-alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- or diar-lower alkyl phosphoryl groups such as diphenylphosphoryl, dibenzylphosphoryl and the like; oxygen-containing heterocyclic alkyl groups such as 5-methyl-2-oxo-2H-1,3-dioxol-4-ylmethyl and like; substituted silyl groups such as trimethylsilyl and the like; etc.

As salts of the compounds of general formula [1], conventionally known salts formed at the position of basic group such as amino groups and the like and acidic group such as hydroxyl group, carboxyl group and the like can be referred to. As the salts formed at the position of basic group, for example, salts formed with mineral acids such as hydrochloric acid, hydrobromic acid, sulfuric acid and the like; salts formed with organic carboxylic acids such as formic acid, acetic acid, citric acid, oxalic acid, fumaric acid, maleic acid, malic acid, tartaric acid, aspartic acid and the like; and salts formed with sulfonic acids such as methanesulfonic acid, benzenesulfonic acid, p-toluenesulfonic acid, mesitylenesulfonic acid, naphthalenesulfonic acid and the like can be referred to. As the salts formed at the position of acidic group, for example, salts formed with an alkali metal such as sodium, potassium and the like; salts formed with an alkaline earth metal such as calcium, magnesium and the like; ammonium salts, salts formed with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-beta-phenethylamine, 1-ephenamine, N,N'-dibenzylethylenediamine and the like; etc.

Some of the alkyl ether derivatives of general formula [I] or salts thereof have isomers such as optical isomer, geometrical isomer, tautomer, etc. In such cases, the present invention involves all those isomers, and further involves hydrates, solvates and all the crystalline forms.

As the alkyl ether derivative or salt thereof used as the ingredient (A), compounds represented by general formula [1] in which the substituents are selected from the following combinations are preferable.

(1) Alkyl ether derivatives or salts thereof in which $R^1$ is a benzothienyl or benzofuranyl group which may be substituted with a group selected from halogen atoms, alkyl groups and phenyl group; $R^2$ is a hydroxyl group; $R^3$ is an alkyl group; $R^4$ is an alkyl group which may be substituted with an alkoxy-substituted phenyl group or $R^3$ and $R^4$, taken in conjunction with a nitrogen atom to which $R^3$ and $R^4$ are linked, form a pyrrolidine ring, piperidine ring, piperazine ring or a morpholine ring; m is 1; and n is 2.

A specific example of such a compound is (benzo[b] thiophen-5-yl)-2-[2-(N,N-diethylamino)ethoxy]ethanol.

(2) Alkyl ether derivatives or salts thereof in which $R^1$ is a benzothienyl or benzofuranyl group which may be substituted with a group selected from halogen atom, alkyl group optionally substituted with hydroxyl group, alkoxy group, carboxyl group, aminocarbonyl group, hydroxyl group, alkylthio group, phenyl group and pyridyl group; $R^2$ is a hydrogen atom; $R^3$ is an alkyl group which may be substituted with a group selected from phenyl group optionally substituted with halogen atom, alkoxy group or nitro group, optionally protected hydroxyl group, alkylamino group and alkynyl group; $R^4$ is an alkyl group which may be substituted with a phenyl group; m is 1; and n is 2 to 3.

A specific example of such a compound is 2-[[3-(2-benzo[b]thiophen-5-ylethoxy)propyl](methyl)amino]-1-ethanol.

(3) Alkyl ether derivatives or salts thereof in which $R^1$ is a benzothienyl or benzofuranyl group which may be substituted with a group selected from halogen atom, alkyl group and phenyl group; $R^2$ is a hydrogen atom; $R^3$ or $R^4$ is an alkyl group which may be substituted with hydroxyl group, optionally protected amino group and alkylamino group, or $R^3$ and $R^4$ represent an azetidine ring, a pyrrolidine ring, a piperidine ring, a piperazine ring or a morpholine ring which is formed by $R^3$ and $R^4$ together with the nitrogen atom to which $R^3$ and $R^4$ are linked; m is 1; and n is 2 to 3.

An example of such a compound is 1-[2-[2-(1-benzothiophen-5-yl(ethoxy]ethyl]-3-azetidinol.

The alkyl ether derivatives of general formula [1] or salts thereof can be produced according to the method described in JP 3-47158A, JP 3-232830A, JP 4-95070A, WO99/31056, WO00/76957, PCT/JP02/10827, etc.

As the compound having an acetylcholine esterase inhibiting activity used in this invention as ingredient (B), for example, the following can be referred to:

Tacrine; the compounds described in JP 1-79151A represented by Donepezil; the compounds described in JP 61-225158A represented by Rivastigmine; the compounds described in JP 62-215527A represented by Galanthamine; the compounds described in U.S. Pat. No. 5,177,082 represented by Huperzine; Ipidacrine; the compounds described in JP 5-140149A represented by Zanapezil; Phenserine; Quilostigmine; Ganstigmine; the compounds described in WO92/18493 represented by Ensaculin; the compounds described in JP 5-279355A represented by T-82; and the like. Among these compounds, those further preferable as ingredient (B) are Tacrine and Donepezil.

In making a pharmaceutical preparation from a composition comprising the alkyl ether derivative of general formula [1] or a salt thereof and a compound having an acetylcholine esterase inhibiting activity or a salt thereof, a pharmaceutical preparation such as tablet, capsule, powder, granule, fine granule, pill, suspension, emulsion, solution, syrup, injection, eye drop and the like can be formed in the usual manner by appropriately using pharmaceutically acceptable assistants such as excipient, carrier, diluent, stabilizer and the like. The pharmaceutical preparation thus formed can be administered orally or non-orally. Although the method of administration, the dosage of administration and the frequency of administration can be appropriately selected in accordance with age, body weight and symptom of the patient, it is conventional in the case of oral administration to an adult person to administer 0.01-500 mg in one to several portions per day.

Although the proportions of the ingredients (A) and (B) may be selected appropriately, the amount of ingredient (B) is 0.0005-1 part by weight per 1 part by weight of ingredient (A).

Although the amounts of ingredients (A) and (B) vary depending on the combination thereof, for example, the amount of ingredient (B) (the compound having an acetylcholine esterase inhibitory activity) may be an amount at which a reaction of the peripheral nervous symptom (predominantly, the reaction caused by the parasympathetic nervous system such as diarrhoea, lacrimmation, salivation, etc.) does not appear significantly. For example, the amount is about 0.05 mg to 10 mg per day in the case of Donepezil, about 1 mg to 120 mg per day in the case of Zanapezil, about 5 mg to 200 mg per day in the case of Tacrine, about 10 mg to 300 mg per day in the case of Ipidacrine, and about 0.5 mg to 20 mg per day in the case of Rivastigmine.

Although the amount of ingredient (A) varies depending on the kind of ingredient (B), namely the compound having an acetylcholine esterase inhibitory activity, it is 0.01 to 500 mg per day.

EXAMPLES

Next, the activating and protecting actions on neurons brought about by combination of an alkyl ether derivative of general formula [1] or a salt thereof and a compound having an acetylcholine esterase inhibiting activity will be mentioned.

Anti-Hypoxic Activity

Compound A1: T-588

Compound A2: 2-[[3-(2-benzo[b]thiophen-5-yl-ethoxy)propyl](methyl)amino]-1-ethanol.1/2fumarate Compound A3: 1-[3-(2-(1-benzothiophen-5-yl)ethoxy)-propyl]-3-azetidinol.maleate Compound B1: Donepezil Compound B2: Tacrine Compound C1: Idebenone Compound C2: SR57746A Test compounds A1, A2, A3, B1 and B2 were put to use after dissolution in distilled water. Test compounds C1 and C2 were put to use after suspending them in 0.5% solution of methylcellulose.

(Testing Method)

The test was carried out according to the method described in Japanese Journal of Pharmacology, Vol. 62, Page 81, 1993.

To one group (6-10 animals) of ddY male mice having an age of 4-5 weeks was orally administered a test compound dissolved in distilled water or suspended in 0.5% methyl cellulose solution. Thirty minutes after the administration, the mice were introduced into a glass container at a volume of 300 mL, and a gaseous mixture composed of 4% of oxygen and 96% of nitrogen was passed though the glass container at a flow rate of 5 L/minute. The period of time from the start of passing the gaseous mixture to the death of the mice was measured. To the control group, distilled water was administered orally.

The anti-hypoxic activity of each test compound was calculated according to the following formula:

(Survival time of mouse in the test compound−administered group/Survival time of mouse in the control group)×100%

The results are shown in Tables 1-3.

TABLE 1

| Compound (1) | Dosage (mg/kg) | Compound (2) | Dosage (mg/kg) | Anti-hypoxic activity (%) |
|---|---|---|---|---|
| Control | — | — | — | 100 |
| Compound A1 | 10 | — | — | 137 |
| Compound B1 | 3 | — | — | 119 |
| Compound B2 | 10 | — | — | 127 |
| Compound A1 | 10 | Compound B1 | 3 | 211 |
| Compound A1 | 10 | Compound B2 | 10 | 172 |

TABLE 2

| Compound (1) | Dosage (mg/kg) | Compound (2) | Dosage (mg/kg) | Anti-hypoxic activity (%) |
|---|---|---|---|---|
| Control | — | — | — | 100 |
| Compound A2 | 10 | — | — | 114 |
| Compound A3 | 10 | — | — | 111 |
| Compound B1 | 3 | — | — | 104 |
| Compound B2 | 10 | — | — | 107 |
| Compound A2 | 10 | Compound B1 | 3 | 168 |
| Compound A2 | 10 | Compound B2 | 10 | 172 |
| Compound A3 | 10 | Compound B1 | 3 | 190 |
| Compound A3 | 10 | Compound B2 | 10 | 149 |

TABLE 3

| Compound (1) | Dosage (mg/kg) | Compound (2) | Dosage (mg/kg) | Anti-hypoxic activity (%) |
|---|---|---|---|---|
| Control | — | — | — | 100 |
| Compound C1 | 100 | — | — | 104 |
| Compound C1 | 300 | — | — | 108 |
| Compound C1 | 300 | Compound B1 | 3 | 100 |
| Compound C2 | 30 | — | — | 100 |
| Compound C2 | 100 | — | — | 123 |
| Compound C2 | 100 | Compound B1 | 3 | 111 |

INDUSTRIAL APPLICABILITY

Anti-hypoxic activity can synergistically be improved by combining the alkyl ether derivative of general formula [1] or a salt thereof with a compound having an acetylcholine esterase inhibitory activity. Accordingly, the combination of this invention is useful as a method for improving the cerebral function. A pharmaceutical composition containing the compound according to the combination of this invention is useful for treatment and prevention of dysfunction of cerebral acetylcholine neurons in the sequela of cerebrovascular dementia, senile dementia, Alzheimer's disease and ischemic cerebral lesion and in the cerebral apoplexy or the memory impairment caused by selective neuronal death.

The invention claimed is:

[1. A pharmaceutical composition comprising the following ingredients (A) and (B):

Ingredient (A): An alkyl ether derivative represented by the following formula:

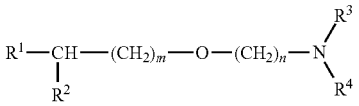

wherein $R^1$ represents a benzothienyl group which may be substituted with a group selected from a halogen atom, an alkyl group, and a phenyl group; $R^2$ represents a hydrogen atom; $R^3$ and $R^4$, each represents an alkyl group, or $R^3$ and $R^4$, taken conjointly with the nitrogen atom to which $R^3$ and $R^4$ are linked, form an azetidine ring; m represents 1; and n represents 2 to 3; or a salt thereof, Ingredient (B): A compound selected from the group consisting of Donepezil and Tacrine.]

[2. A method of preparing a medicament comprising combining the following ingredients (A) and (B), Ingredient (A): An alkyl ether derivative represented by the following formula:

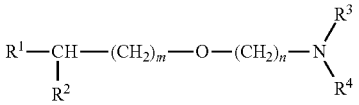

wherein $R^1$ represents a benzothienyl group which may be substituted with a group selected from a halogen atom, an alkyl group, and a phenyl group; $R^2$ represents a hydrogen atom; $R^3$ and $R^4$, each represents an alkyl group, or $R^3$ and $R^4$, taken conjointly with the nitrogen atom to which $R^3$ and $R^4$ are linked, form an azetidine ring; m represents; and n represents 2 to 3; or a salt thereof, Ingredient (B): A compound selected from the group consisting of Donepezil and Tacrine.]

[3. A pharmaceutical composition as claimed in claim 1 wherein the pharmaceutical composition is administered to a patient to treat Alzheimer's disease.]

[4. A method of treating Alzheimer's disease comprising administering the pharmaceutical composition of claim 1 to a patient in need thereof.]

5. The pharmaceutical composition as claimed in claim [1] *9*, wherein said ingredient (A) is [1-[3-(2-(1-benzothiophen-5-yl)ethoxy)propyl]-3-azetidinol.or] *1-[3-(2-(1-benzothiophen-5-yl)ethoxy)propyl]-3-azetidinol or* a salt thereof.

6. The pharmaceutical composition as claimed in claim [1] *9*, wherein said ingredient (A) is [1-[3-(2-(1-benzothiophen-5-yl)ethoxy)propyl]-3-azetidinol.maleate] *1-[3-(2-(1-benzothiophen-5-yl)ethoxy)propyl]-3-azetidinol maleate*.

7. The method as claimed in claim [2] *10*, wherein said ingredient (A) is [1-[3-(2-(1-benzothiophen-5-yl)ethoxy) propyl]-3-azetidinol.or] *1-[3-(2-(1-benzothiophen-5-yl) ethoxy)propyl]-3-azetidinol or* a salt thereof.

8. The method as claimed in claim [2] *10*, wherein said ingredient (A) is [1-[3-(2-(1-benzothiophen-5-yl)ethoxy) propyl]-3-azetidinolmaleate] *1-[3-(2-(1-benzothiophen-5-yl)ethoxy)propyl]-3-azetidinol maleate*.

*9. A pharmaceutical composition comprising the following ingredients (A) and (B):*

*Ingredient (A): An alkyl ether derivative represented by the following formula:*

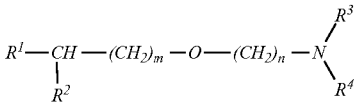

*wherein $R^1$ represents a benzothienyl group which may be substituted with a group selected from a halogen atom, an alkyl group, and a phenyl group; $R^2$ represents a hydrogen atom; $R^3$ and $R^4$, taken conjointly with the nitrogen atom to which $R^3$ and $R^4$ are linked, form an azetidine ring which may be substituted by a hydroxyl group; m represents 1; and n represents 2 to 3; or a salt thereof,*

*Ingredient (B): A compound selected from the group consisting of Donepezil and Tacrine.*

*10. A method of preparing a medicament comprising combining the following ingredients (A) and (B),*

*Ingredient (A): An alkyl ether derivative represented by the following formula:*

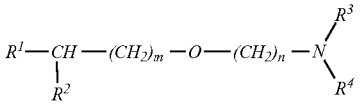

*wherein $R^1$ represents a benzothienyl group which may be substituted with a group selected from a halogen atom, an alkyl group, and a phenyl group; $R^2$ represents a hydrogen atom; $R^3$ and $R^4$, taken conjointly with the nitrogen atom to which $R^3$ and $R^4$ are linked, form an azetidine ring which may be substituted by a hydroxyl group; m represents 1; and n represents 2 to 3; or a salt thereof,*

*Ingredient (B): A compound selected from the group consisting of Donepezil and Tacrine.*

*11. A pharmaceutical composition as claimed in claim 9, wherein the pharmaceutical composition is administered to a patient to treat Alzheimer's disease.*

*12. A method of treating Alzheimer's disease comprising administering the pharmaceutical composition of claim 9 to a patient in need thereof.*

* * * * *